United States Patent [19]

Horn et al.

[11] Patent Number: 4,800,166

[45] Date of Patent: Jan. 24, 1989

[54] METHOD AND APPARATUS FOR MONITORING THE AUTOMATED SYNTHESIS OF PEPTIDES

[75] Inventors: Marcus J. Horn, Cambridge; Joanne Recchia, Norwood, both of Mass.

[73] Assignee: Applied Protein Technologies, Inc., Cambridge, Mass.

[21] Appl. No.: 871,513

[22] Filed: Jun. 6, 1986

Related U.S. Application Data

[63] Continuation-in-part of Ser. No. 725,213, Apr. 19, 1985, Pat. No. 4,701,304.

[51] Int. Cl.$^4$ ............................................. G01N 33/68
[52] U.S. Cl. ...................................... 436/55; 422/62; 422/81; 436/89; 935/87; 935/88
[58] Field of Search ........................... 436/89, 90, 55; 422/116, 81, 131, 62; 260/112.5 R; 935/87, 88

[56] References Cited

U.S. PATENT DOCUMENTS 3,862,113  1/1975  Riniker et al.
3,997,516 12/1976  Nishimura

OTHER PUBLICATIONS

CA 101:152329f—Barlos.
CA 78:84822r—Losse.

Primary Examiner—Michael S. Marcus
Attorney, Agent, or Firm—Nutter, McClennen & Fish

[57] ABSTRACT

A method for monitoring a solid-phase peptide synthesis for free amino ends of unreacted peptide chains, the monitoring occurring at the end of each addition of a blocked amino acid to the peptide chains which are anchored to the solid phase. The method includes reacting the solid phase with a monitoring agent that forms a covalent bond with unblocked amino groups. The solid phase is then washed to remove the unreacted monitoring agent. A cleaving reagent is then used to selectively remove the covalently bound monitoring reagent from the ends of the unblocked peptide chains, while leaving the blocked chains intact. The amount of monitoring agent thus removed is then quantitatively measured to determine what proportion of the initial peptide chains failed to react with the blocked amino acid.

Preferred monitoring agents for use in this process include trityl (triphenylmethyl) -based groups, and particularly preferred agents are trityl, monomethoxytrityl, dimethoxytrityl, and trimethoxytrityl chlorides.

16 Claims, 3 Drawing Sheets

METHOD AND APPARATUS FOR MONITORING THE AUTOMATED SYNTHESIS OF PEPTIDES

CROSS-REFERENCES TO RELATED APPLICATIONS

This application is a continuation-in-part application of prior U.S. Application Ser No. 725,213, filed on Apr. 19, 1985, for Method and Apparatus for Automated Synthesis of Peptides, now U.S. Pat. No. 4,701,304.

FIELD OF THE INVENTION

The invention relates to a method and apparatus for automating the manufacture of a substance involving a sequence of chemical reactions, and more particularly to a system for the synthesis of organic compounds, such as peptides and proteins. The invention is especially suited to the solid-phase synthesis of peptides, wherein each sequence of chemical reactions results in the addition of a new amino acid to a peptide anchored to the solid phase. According to the invention, each amino acid addition is monitored for completeness before the next amino acid is added to the peptide.

BACKGROUND OF THE INVENTION

The solid-phase synthesis of a peptide involves stepwise additions of amino-terminus-blocked amino acids to a peptide chain, the carboxyl terminus of which is anchored to a solid support. The synthesis begins with the amino acid at the carboxyl-terminal of the chain and proceeds with single- amino acid additions to the successive amino termini of the chain. It is initiated by covalently attaching the carboxyl terminus of the carboxyl-terminal amino acid to an insoluble solid support, which is typically a matrix of resin beads that are large enough to be separated from the liquid phase by filtration.

The next amino acid to be added is first protected at its amino terminus with a blocking group, such as butyloxycarbonyl (BOC), so that this terminus is no longer reactive with the reagents that promote the formation of peptide bonds. The blocked amino acid is then reacted, in the presence of a condensing agent, such as dicyclohexyl-carbodiimide, with the anchored amino acid to form a peptide bond between the carboxyl terminus of the bocked amino acid and the amino terminus of the anchored amino acid.

The resulting peptide chain (which now consists of two amino acids) remains anchored to the insoluble resin, and is therefore easily separated from the reactants by thorough washing. The blocking group is then removed from the amino terminus of the amino terminal amino acid of the peptide chain by acidification (using trifluoroacetic acid, for example,) so that the peptide is now terminated with a free amino group that is ready to react with the next blocked amino acid to be added to the chain.

In similar fashion, subsequent amino acids are added to the anchored peptide chain to build the complete peptide. After the peptide is completed, it is removed from the insoluble resin and isolated.

In reality, peptide synthesis is more complicated. For example, the reagents used to form the peptide bond also react with side groups of some of the amino acids (approximately twenty different amino acids are routinely used to form a peptide). Therefore, these sensitive side groups must also be protected with special blocking groups during the entire synthesis of the peptide. These special blocking groups must be stable under the conditions of deblocking of the amino-terminal termini of the peptide chains and must also be readily removed from the completed peptide.

Also, each amino acid has its own individual optimum reaction kinetics, and these kinetics are affected by the environment surrounding the amino terminal of the peptide chain. This environment is determined not only by the amino acid at the amino terminus itself, but also by the other amino acids in the peptide chain and their interactions with both the solid and the liquid phases.

Specifically, the different amino acid configurations may cause the peptide to bend and fold three-dimensionally, and thus the free amino terminus of the amino terminal amino acid may be hindered sterically from reacting with the blocked amino acid to be added to the peptide chain. Also, the different amino acids in the chain have different hydrophobic/hydrophilic effects on the surroundings of the free amino terminal, particularly, on the solvation of the resin itself, which affect the accessibility of the free amino terminus to the liquid reactants and, thus, the reaction rate. Therefore, since the sequence of each peptide to be synthesized is different, the optimum reaction conditions for each amino acid addition are difficult to predict.

As a result, the reaction at each step of the synthesis seldom goes to completion, that is, the yield is generally somewhat less than 100%. Obviously, the yield at each step must be very high if a peptide chain of substantial length is to be prepared in substantial quantity. For example, a yield of 99.0% per step results in a product yield of only 81% after 20 amino acid additions, while a yield per step increase of only 0.5% (to 99.5% per step) results in a product of 90% yield—almost 10% higher. Another increase of only 0.4% per step—to 99.9% results in a 98% ultimate yield. The yield represents not only the total amount of the resulting peptide, but also its purity. The purity is important because it is difficult and costly to separate the desired peptide from undesidred peptides that vary in only a few amino acids, and which arise from incomplete reactions. The total amount is important because if the yield is low, the amount of expensive starting materials must be increased accordingly.

A system for synthesizing these peptides must therefore accomodate the large number of different steps and the varying reaction conditions. It also must be constructed to minimize cross-contamination among the amino acids, as well as the solvents and reagents used in the process. Ideally, the system should further include a method and apparatus for monitoring the completeness of each amino acid addition before the next amino acid is added to the peptide chain. If the results from the monitoring indicate that the amino acid addition has not proceeded to a desired level of completeness, the previous addition reaction may be repeated until the desired level is attained. Such a system ensures the highest possible yield at each step.

Prior apparatus for synthesizing peptides can be divided into two types: column synthesizers, such as described in U.S. Pat. No. 4,362,699, and shaker/reactor vessels, which are described in U.S. Pat. Nos. 4,362,699, 3,531,258, 3,647,390, and 3,557,077. Prior monitoring methods and the advantaegs and disadvantages of each method are summarized in "Selected Methods for Monitoring a Solid-Phase Peptide Synthesis", G. Barany and B. Merrifield, The Peptides, V.2., 1979, pp. 150–154.

In the column synthesizers, solid support beads to which the growing peptide chains are attached, are packed into a column. The reagents, solvents, and amino acids required for synthesizing the peptide are reacted with the solid support by passing them sequentially through the column. To obtain reasonable flow rates, these column synthesizers are operated under high pressure, usually greater than 200 psi. With unidirectional flow through the column, the high pressure may compress the solid supports, thus causing increased back pressure and pumping problems. These pressure problems require that special precautions be taken in the system design.

The prior shaker/reactor systems contain filters made from glass frits for retaining a particulate insoluble matrix in a reactor vessel while allowing passage of liquid and gas. Generally, these reactor vessels have separate inlets and outlets for unidirectional flow through the reactor and its filter, such as described in U.S. Pat. No. 3,521,258, to Merrifield et al., and in U.S. Pat. No. 3,557,077 to Brundfeldt et al.

During the various intermediate steps required for each amino acid addition, the different solvents cause the solid support to swell and shrink. The shrunken beads may enter the pores in the filter during one step, and swell during a subsequent step, thereby trapping the beads in the filter. Since flow through the filter is unidirectional, the trapped beads are not removed from the filter, and eventually, during the course of peptide synthesis, they may accumulate in sufficient quantity to impede flow through the filter. Also, clogging of the filter makes the trapped beads at least partially inaccessible to the reaction solvents and reagents, resulting in incomplete reactions at each step.

In the Merrifield Pat. No. 3,521,258, this clogging of the filter causes a backpressure buildup in the system that makes it difficult to obtain a closely metered flow into the reactor. Close metering is important because, with an increase in the degree of uncertainty in the transfer, a corresponding increase in the amount of expensive reagents which must be transferred to compensate for this uncertainty.

There are other drawbacks in these prior systems. For example, in the Merrifield Patent, crosscontamination between solvents and reagents in the selective valves and pumps is a problem. Also, this device cannot accomodate a wide range of reaction volumes because the metering pump is adjustable only over a relatively narrow volume range. Thus, it cannot be used to produce both analytical (small) and commercial (large) quantities of peptides.

Kubodera et al., U.S. Pat. No. 3,647,390, describes a system that avoids clogging of the filter. The reaction vessel has a single port for both inflow and outflow. There is a single filter between this port and a reaction chamber. Thus each time liquid ingredients or reagents are added to the vessel, their flow through the filter tends to dislodge matrix beads that were retained on the filter during the preceding removal of liquid from the vessel. In Kubodera et al., liquid from the reservoirs is transferred to an intermediate metering vessel, and subsequently, from the intermediate metering vessel to the reaction vessel. The metering is accomplished by drawing a vacuum on a vacuum chamber, and connecting the chamber to the intermediate metering vessel. The resulting pressure decrease in the intermediate metering vessel causes transfer of liquid from the reservoir to the intermediate metering vessel until the pressure in the intermediate metering vessel and the vacuum chamber increase to standard pressure. Thus the amount of liquid transferred is directly related to the volumes of the intermediate metering vessel and the vacuum chamber.

This system is cumbersome in that a significant and high vacuum must be drawn on the vacuum chamber for accurate metering of the various liquids. Also, it is difficut to vary the amount drawn to cope with different size reaction vessels, or different quantities or amounts. Essentially, one must change to different-size vacuum chambers. This system also presents a significant likelihood of cross-contamination in the intermediate metering vessel, because it is difficult to completely remove the various liquids from the walls of the intermediate metering vessel before subsequent liquids are introduced.

Of the various methods for monitoring peptide synthesis, for reasons of sensitivity, the ideal methods assay the solid phase for the unreacted, or "free" amino groups at the amino terminus of the anchored peptide chains. Furthermore, these ideal methods should not destroy the peptide chains or interfere with the synthesis of the peptides. The known methods that meet these requirements involve titration of the resin-bound amino groups with salt-forming reagents and quantitation of the amount of resin-bound reagent either potentiometrically or spectrophotometrically.

These titration methods utilize three different reagents: pyridine hydrochloride, perchloric acid or picric acid. In the pyridine hydrochloride method, free amino groups on the solid phase are converted to a hydrochloride salt with pyridine hydrochloride in methylene chloride. The chloride is subsequently eluted from the solid phase to the liquid phase, the liquid phase is separated from the solid phase and the level of chloride ion in the liquid phase is determined potentiometrically. In the perchloric acid method, the free amino groups on the solid phase are determined by direct potentiometric titration of the solid phase by insertion of an electrode directly into the reaction vessel. In the picric acid method, picrate salts of any free amino groups on the solid phase are formed with picric acid, a readily detected chromophore. The picrate ion is subsequently eluted from the solid phase to the liquid phase, the liquid phase is separated from the solid phase, and the level of the picrate ion in the liquid phase is determined spectrophotemetrically.

These titration methods have some disadvantages. The acids used in the pyridine hydrochloride titration can remove some of the amino-blocking groups. In the perchloric acid method, some of the acid sensitive groups may be lost and the amino groups can become permanently acetylated. In the picric acid method, the chromophore reacts stoichiometrically with the amino acid histidine, including its protected forms. Thus, although this increased reactivity can be accounted for by corresponding predictable increasess in the background, the increased background destroys the sensitivity of the assay for free amino ends when peptides containing histidine are monitored. This lack of sensitivity is alleviated to some extent by the use of immidazolium picrate, which reacts less strongly than picric acid with histidine residues.

Also, because the monitoring agents used in these titration methods involve ionic interactions, the agents interact to some extent with the other amino acids in the peptide chain. Therefore, as the peptide chain length increses, so do the number of interactions. The consequence is higher backgrounds, more false positives, and lower sensitivity.

SUMMARY OF THE INVENTION

Accordingly, the invention aims to provide a shaker-reactor type system for automated synthesis of peptides which accurately meters flow of the various liquids into the shaker/reactor.

Another object of the invention is to provide such a system which is adaptable to metering different quantities of different reagents.

Yet another object of the invention is to provide such a system wherein the reagents, solvents and amino acids may be sequentially transferred to a reaction vessel with minimal cross-contamination.

A further object of the invention is to provide a system which can accommodate synthesis of both large and small quantities of peptides.

A still further object of the invention is to provide a such a system wherein each step of the reaction is monitored for degree of completion.

Yet another object of the invention is to provide a monitor and a monitoring method for such a peptide synthesizing system that is sensitive, quantitative, and reproducible.

A further object of the invention is to provide a monitor and monitoring method for such a peptide-synthesizing system that is reversible, and nondestructive of the peptide chains.

Other objects will, in part, be obvious and will, in part, appear hereinafter.

The invention broadly comprises a system maintained under a constant reference pressure, and including a reaction vessel that has a single port for both injection and withdrawal of the various fluids used in the peptide synthesis sequence. The system also includes a volume-displacement pump, specifically a piston-type syringe, for decreasing the pressure in the reaction vessel by removing a controlled volume of gas from the reaction vessel as the first part of each injection step to reduce the pressure within the vessel. This is followed by connection of a selected reservoir to the reaction vessel and flow from the reservoir to the vessel resulting from the pressure differential between the vessel and the reservoir. As soon as the pressure in the reaction vessel has returned to the equilibrium reference level, the transfer is complete.

Removal of a controlled volume of gas from the reaction vessel does not require the evacuation of a chamber and thus can be performed easily without using a high vacuum. The amount of liquid transferred is easily adjustable to accomodate different amounts of selected reagents as well as to accomodate synthesis of different peptide quantities. Transfer is performed directly into the reaction vessel without the use of an intermediate chamber. Thus, the transfer system is easily cleaned to prevent cross-contamination between amino acids, solvents and reagents. Moreover, it lends itself to automatic operation. This is important in peptide synthesis because it takes several hours of reaction time to add even one amino acid to the chain.

The system further comprises a yield monitor which determines the yield after each addition of a blocked amino acid. The monitor utilizes a class of compounds that (1) covalently and specifically bind to free amino groups under certain reaction conditions, and (2) are selectively removed from these same amino groups under different reaction conditions, without removing other blocking or protecting groups that are present on the peptide chains. This class of compounds is also readily detected spectrophotometrically.

Such an agent has not been developed thus far, apparently on the belief that a monitoring agent that covalently attaches to free amino groups could not be removed from these amino ends without also removing the other amino-blocking groups.

Briefly, the monitor works as follows. After each addition of a blocked amino acid to the anchored peptide chains (but before deblocking), the solid phase is covalently reacted with a reversibly-binding monitoring agent. The solid phase is then thoroughly washed, and the monitoring agent is selectively removed from the solid phase under conditions that leave the blocked ends of the completed peptide chains intact. The monitoring agent is now in the liquid phase, which is separated from the solid phase. The presence of the monitoring agent in the liquid phase is detected by measuring the absorbance of the liquid phase, and the level of monitoring agent can be quantitated. This level corresponds directly to the number of free reactive amino ends remaining on the anchored peptide chains. Thus, it provides a means for determining the yield of each amino acid addition.

Because the monitoring method does not remove existing blocking groups, when the yield is not at an appropriately high level, the previous amino acid addition can be repeated as many times as necessary to attain the desired yield. Because the monitoring agent is specific for free amino groups, and reacts minimally with side groups of other amino acids of the peptide chain, the background "noise" of the reaction is very low, and remains low even as the peptide chain length increases. Accordingly, the sensitivity of detecting free amino groups is much higher with our covalently-bonded monitoring agents than with the previous ionically-bonded monitoring agents.

For a fuller understanding of the nature and objects of the invention, reference should be had to the following detailed description, taken in connection with the accompanying drawing figures.

Figure 3:
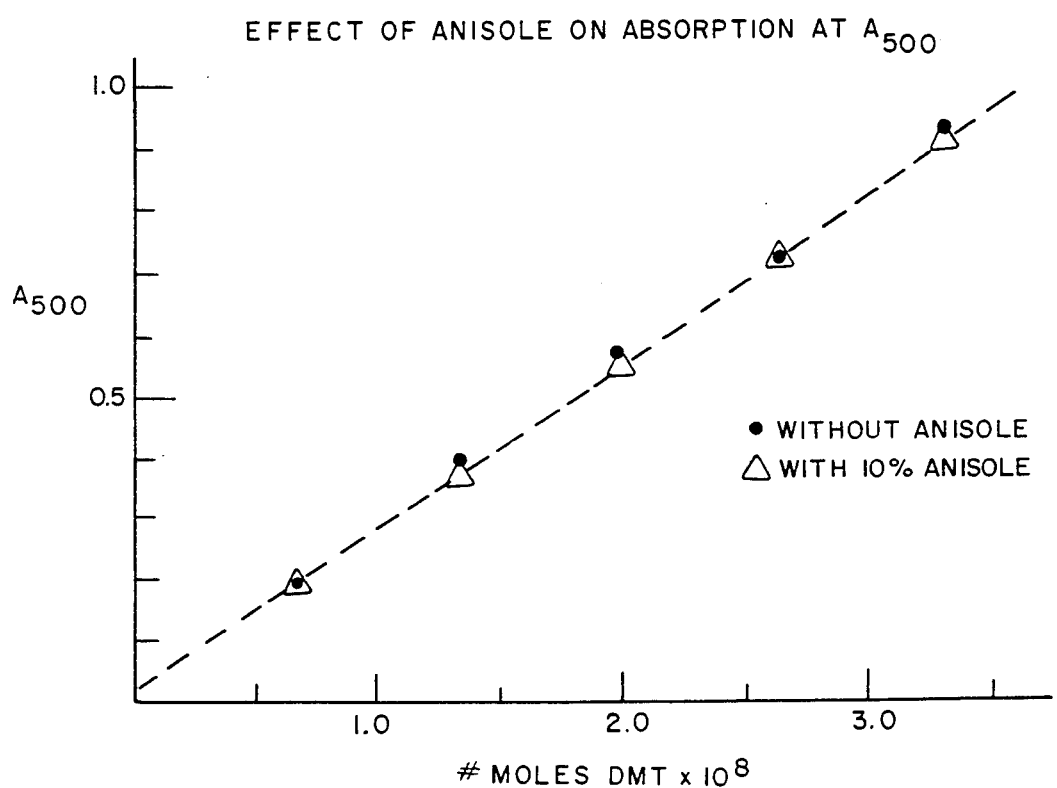

FIG. 3 represents an absorbance profile for dimethoxytrityl chloride in a solution comprising 3% trichloroacetic acid in dichloroethane. The points designated with circles (●) represent absorbance of the dimethoxytrityl group in the solution without anisole and the points designated with triangles (▲) represent absorbance values of the dimethoxytrityl group in the solution further comprising 10% anisole.

Figure 4A:
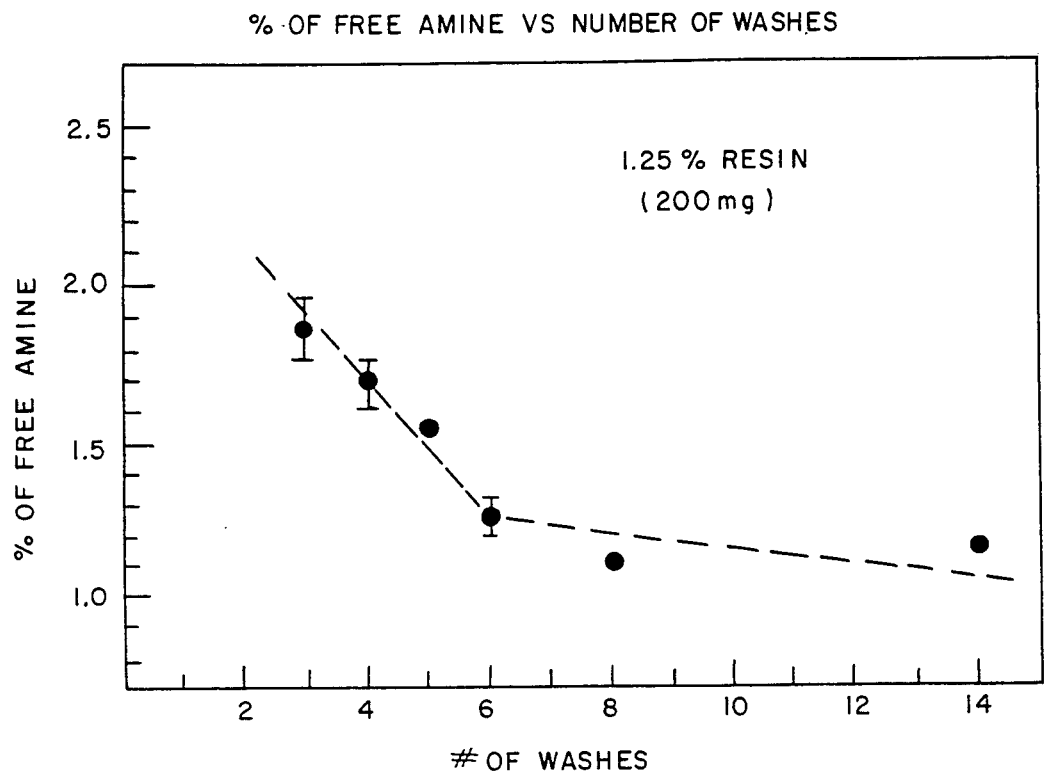
Figure 4B:
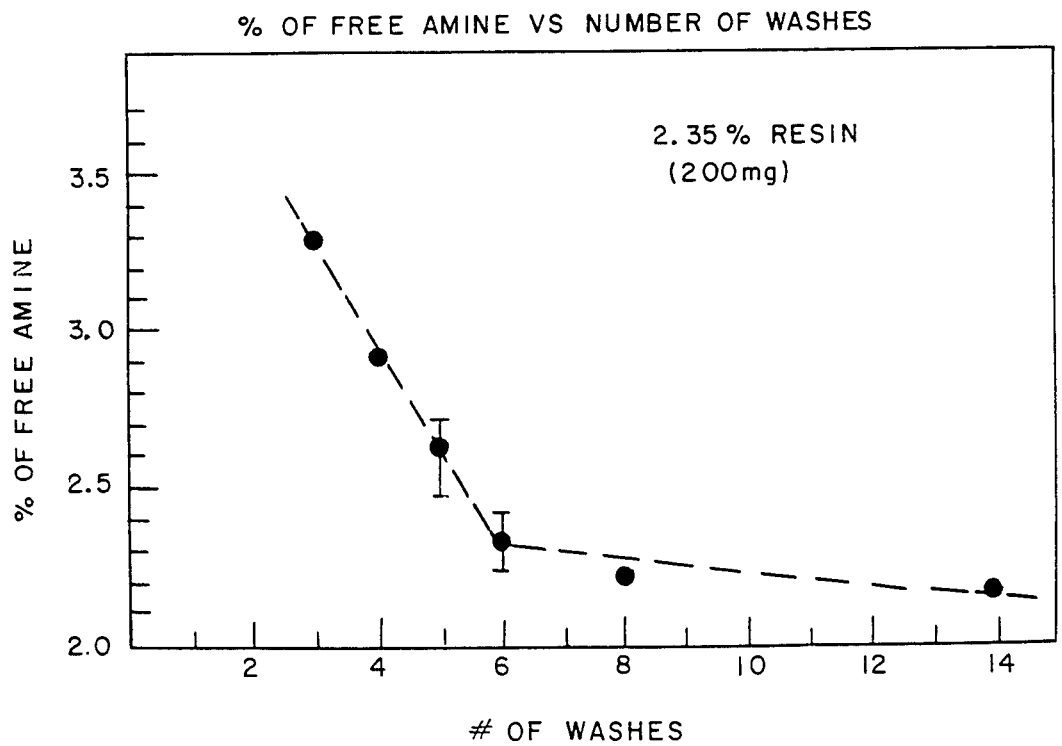

FIGS. 4A and 4B represent graphically the effects of the washing solution on a solid phase that was previously reacted with dimethoxytrityl chloride. The percent free amine on the solid phase was plotted against the number of one-minute washes with a washing solution comprising 1mM hydroxybenzotriazole and 1% trifluoroethanol in dichloroethane. FIG. 4A represents the washing profile obtained with a solid phase resin having 1.25% free amine. FIG. 4B represents the washing profile obtained with a solid phase resin having 2.35% free amine.

DESCRIPTION OF THE PREFERRED EMBODIMENT

Figure 1:
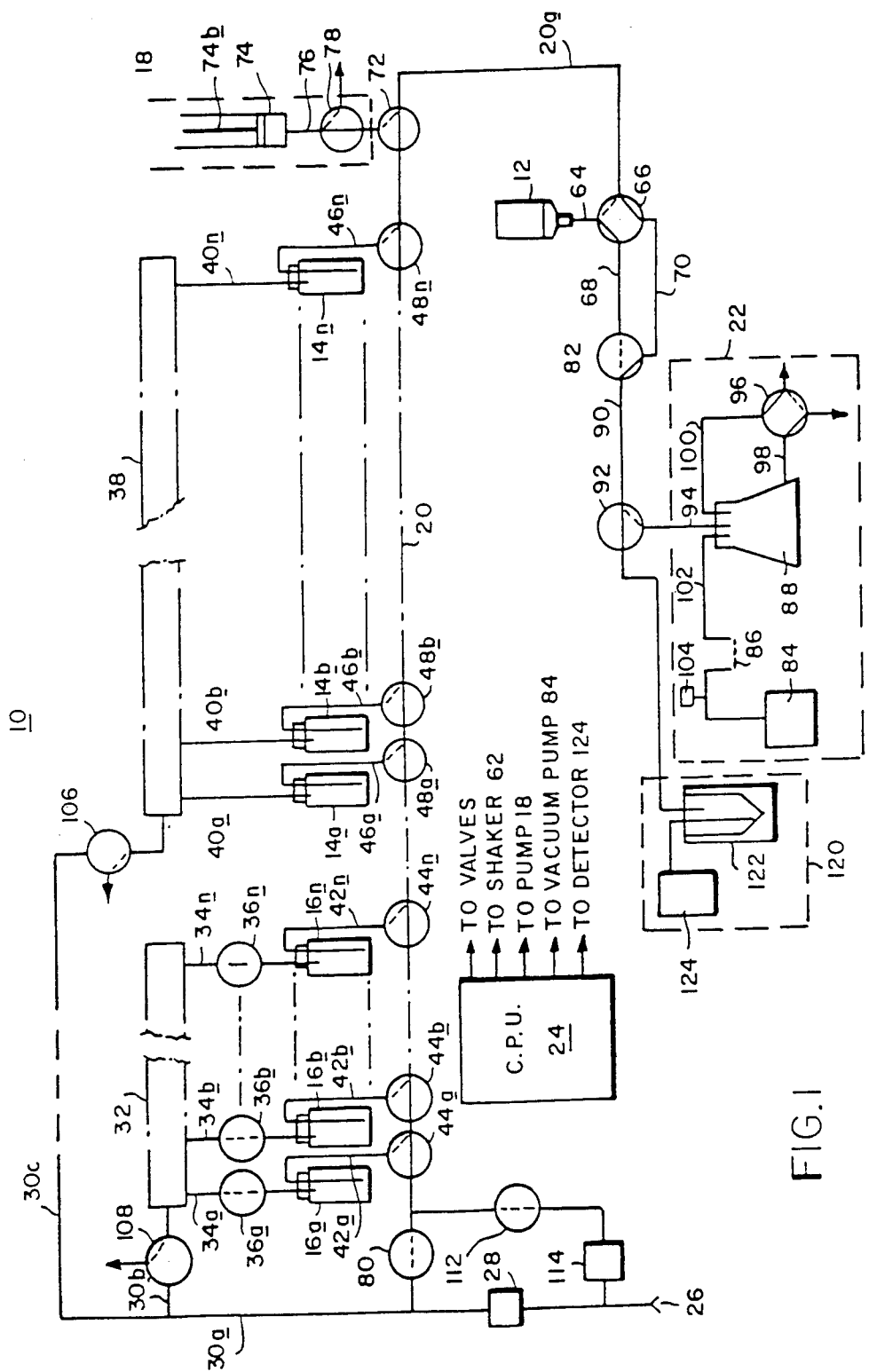
FIG. 1 is a schematic drawing of the overall apparatus embodying the invention.

Referring to FIG. 1, a system 10 for synthesizing peptides broadly comprises a reaction vessel 12 in which the peptide chains are manufactured; a plurality of amino acid reservoirs 14a-14n, each containing an amino acid Aa-An, the "building-block" subunits of the peptide; a plurality of reagent reservoirs 16a-16n, each containing a solvent or reagent Ra-Rn for promoting the synthesis of the peptide; a volume displacement pump 18 for removing predetermined volumes of gas from the vessel 12; a main transfer line 20 for transferring reagents and amino acids from the reservoirs to the reaction vessel; an exhaust system 22 for removing gaseous and liquid wastes from the vessels and the transfer line; and a central processor 24, which controls operation of the various components of the system.

All parts of the system that contact the reagents and solvents are made of chemically resistant materials, such as teflon, glass, or stainless steel.

A reference pressure P is supplied to the system by a nitrogen pressure source 26 and a pressure regulator 28. This pressure P is typically 2-5 p.s.i., but can be set to any pressure, preferably above atmospheric. It is applied from source 26 to reservoirs 16a-16n through lines 30a and 30b, which feed into a manifold 32. The manifold 32, in turn, connects to the reservoirs 16a-16n through a plurality of lines 34a-34n. The lines 34a-34n are further equipped with corresponding valves 36a-36n. These valves 36a-36n, in their normal or deactuated connections, close the reservoirs to the manifold 32 and the pressure source 26. During pressurization of the reservoirs 16a-16n, valves 36a-36n are actuated and deactuated independently to equilibrate selected reservoirs with the pressure P. The independent valve actuation isolates each of the reservoirs and thereby prevents cross-contamination which would result from backflow of volatile reagents Ra-Rn to the manifold if the reservoirs were all connected to the manifold 32 at the same time.

The valves 36a-36n, as well as the other valves in the system 10, are pneumatically- rather than electrically-actuated to prevent chemically-induced corrosion of the valves by the liquids transferred therethrough. The normal, or deactuated connections of the valves are represented in the drawing as solid lines, and the actuated connections of the valves are represented as dotted lines. Pressure for the operation of the pneumatically-actuated valves is supplied by the pressure source 26, under separate regulation, and is controlled by individually electrically-energized actuators (not shown).

Similarly, the reference pressure P is applied to the amino acid reservoirs 14a-14n through lines 30a and 30c, and a second manifold 38. Manifold 38 connects to the reservoirs 14a-14n through lines 40a-40n, respectively. The lines 40a-40n are not equipped with valves similar to the valves 36a-36n, because amino acids are not volatile, and consequently there is little danger of cross-contamination from volatiles backflowing into the manifold 38.

The reservoirs 16a-16n are connected to the main transfer line 20 through corresponding branch lines 42a-42n and valves 44a-44n. Similarly, the reservoirs 14a-14n are connected to the main transfer line 20 through corresponding branch lines 46a-46n and valves 48a-48n. The valves 44a-44n and 48a-48n are connected in series along main transfer line 20, with their normal connections being "open" along main line 20 and "closed" to their respective reservoirs 16a-16n and 14a-14n.

Figure 2:
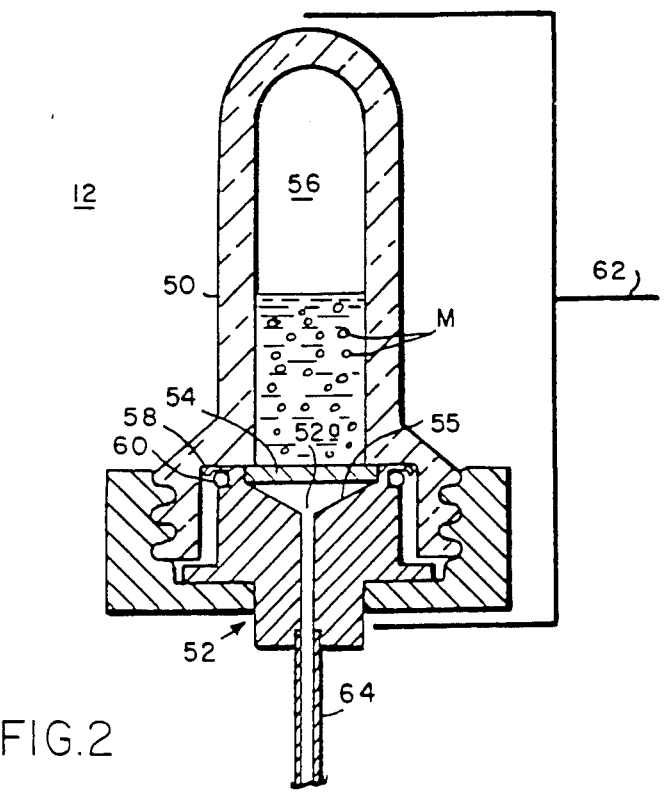
FIG. 2 is a sectional view of the reaction vessel used in the apparatus of the invention.

The reaction vessel 12 is shown in more detail in FIG. 2. It comprises an upper section 50, threaded to a lower section 52. Lower section 52 has a single port 52a, and houses a porous filter 54 extending across the vessel 12 and thus across the port 52a. With the upper section 50, the filter 54 defines a reaction chamber 56. The chamber 56 encloses an insoluble support matrix M, typically in the form of polystyrene or other resin beads, to which is attached the carboxyl-terminal amino acids of the peptide chains to be built. Gas and liquid flow into and out of the chamber 56 through port 52a and filter 54.

More specifically, the filter 54 fits snugly within a preformed well 55 in the lower section 52. The well 55 is tapered towards the port 52a to ensure communication between the port and the under surface of the filter 54. A seal is provided by a gasket 58 and a resilient O-ring 60. When the upper section 50 is threaded to lower section 52, a shoulder 50a fits tightly against the gasket 58, and compresses the O-ring 60. This tightens the O-ring around the filter 54 to hold the filter securely in place during flow therethrough into the chamber 56.

The insoluble support matrix M to which the peptide chains are anchored is typically made from a resin such as polystyrene or polyacrylamide, but it may also be made of any other suitable material, such as acrylamide-impregnated silica or porous glass, to which the peptide chains may be attached but which is otherwise inert in the context of the reactions carried out in the vessel 12.

The porosity of filter 54 is such that it retains the matrix M within the chamber 56, while allowing passage of liquid and gas through the filter 54 into and out of the chamber 56. Thus, the matrix M, and its anchored peptide chains, can be easily separated by the filter from the liquid and gaseous reactants and byproducts involved in the processes that take place in the vessel 12.

The vessel 12 is further equipped with a shaker 62, shown schematically in FIG. 2, for slow reciprocation through an angle of approximately 180°, so that the matrix M beads, and the peptide chains attached to them are throughly mixed with the liquid solvents, reagents or amino acids in the chamber 56. The beads of matrix M can become "sticky" in some of the organic solvents used, and resultantly adhere to the walls of chamber 56. Therefore, in order to ensure that all beads of the matrix M, including beads that are stuck to the chamber wall, come in contact with the liquid reactants of each step of the overall process, vessel 12 is sized such that its total volume capacity is less than twice the liquid reaction volume. This allows all of the matrix beads, including beads stuck to the walls of the chamber to contact the liquid reactants in the vessel during each shaking cycle.

Returning to FIG. 1, the vessel 12 is connected to the other parts of the system 10 through its port 52a by a flexible transfer line 64 and a valve 66. When actuated, valve 66 connects the reaction vessel 12 solely to the main transfer line 20. When deactuated, valve 66 forms dual connections: it connects the reaction vessel 12 with a waste removal line 68, and, at the same time, it connects the main transfer line 20 with a second waste removal line 70 which bypasses reaction vessel 12.

Transfer of solvents, reagents, and amino acids from the reservoirs 16a-16n and 14a-14n to the reaction vessel 12 is accomplished by the volume displacement pump 18, which taps directly to main transfer line 20 through a valve 72. Valve 72 has its normal connection closed to pump 18 and open along transfer line 20.

Pump 18 comprises a rigidly mounted syringe 74 having a plunger 74b attached to an actuator. The syringe 74 has a single port 74a connected to the valve 72 by a line 76 and a valve 78.

To begin a transfer, the system 10 is equilibrated to the reference pressure P. The vessel 12 is pressurized to the reference pressure through line 20 by actuating the valve 66, and also a valve 80 that connects the main transfer line 20 to the reference pressure from source 26. The valve 80 is then deactuated. At this time, the pump 18 is at its is at its zero-position, with the syringe plunger 74b at its lower most position.

Next the valve 72 is actuated so that the interior of the syringe 74 and the vessel 12 communicate with each other through the valve 66 and the portion 20a of the line 20 between them. Then the plunger 74b is withdrawn to a predetermined volume. This withdrawal increases the effective volume of the vessel 12 in the amount of the volume within the syringe, and, thus, lowers the pressure in the vessel 12.

Transfer of a selected amino acid, e.g. amino acid Aa in reservoir 14a, is then effected by deactuating the valve 72, and actuating the valve 48a, thus connecting the selected reservoir 14a to the vessel 12. The pressure returns to equilibrium by transferring a volume of liquid Aa from the reservoir 14a to the vessel 12.

There is a simple relationship between the displacement of the pump 18 and the volume of liquid transferred to the reaction vessel 12. Assume, for example, that the plunger 74 is displaced from its zero-volume position to a point where the volume in the syringe equals the gas volume of the vessel 12. Then, neglecting the small volume in the portion 20a of line 20 between the pump 18 and the vessel 12, one-half the gas in the vessel 12 will transfer to the pump 18. This is equivalent to evacuating one-half the vessel 12 and maintaining the other half at its original, i.e. reference, pressure. Accordingly, when a reservoir is then connected to the vessel 12, the quantity of liquid transferred to the vessel 12 is one-half the volume of the vessel.

Similarly, if the volume displacement of the pump 18 is one-half the gas volume of the vessel 12, the gas in the vessel 12 will divide between the vessel 12 and the pump 18 in the ratio 2:1, i.e., one-third of the gas in the vessel 12 will transfer to the pump 18. Accordingly, the volume of liquid subsequently transferred from a reservoir will be one-third the gas volume of the vessel 12.

Greater accuracy in liquid transfers to the vessel 12 can be obtained by accounting for the zero-position volume of the pump 18, i.e. between the valve 72 and the bottom of the plunger 74b in its lower most position, the volume of the line portion 20a and the portion of the line 20 between the selected reservoir and the valve 72. The volume of the line portion 20a and the zero-position volume of the pump 18 can be considered as part of the gas volume of the vessel 12 in calculating the stroke of the pump 18.

On the other hand, the gas in the line 20 portion between the selected reservoir and the valve 72 is transferred to the vessel 12 in advance of the liquid. Accordingly, since this gas is at the reference pressure immediately prior to the transfer from that reservoir, the volume of this portion of the line 20 should be added to the volume of liquid to be transferred in calculating the stroke of the pump 18.

Additionally, when the vessel 12 reaches pressure equilibrium at the end of a liquid transfer, the transfer line portion 20a will contain some of the liquid retrieved from the selected reservoir. A valve 112, which taps into the line 20 between the valve 80 and the reservoir valves 44a–44n, and which connects the line 20 to the pressure source 26 at a point before the pressure regulator 28, is therefore actuated to apply an elevated pressure to the line 20 to force this liquid into the vessel 12. This elevated pressure is regulated by a second pressure regulator 114.

The valve 66 is then deactuated, closing the vessel 12 to the main line 20 and, at the same time, shunting the line 20 to the waste removal line 70. When valve 66 is deactuated, vessel 12 communicates directly to one end of the waste removal line 68, which is closed to the system 10 at this time because of a deactuated valve 82 located at the other end of the line 68. At this time (or subsequently), the plunger 74b of the pump 18 is retrieved to its initial (bottom) position. During this displacement of the plunger, the valve 78 is actuated to vent the pump to the atmosphere.

The reaction vessel 12 is then reciprocated by the shaker 62 for a short time so that the liquid amino acid introduced the vessel 12 mixes with the solid matrix M. Then, the reagents or solvents, for example reagent Ra in reservoir 16a, that are required to promote attachment of the amino acid to the free end of the peptide chain, (or, initially, in the case of the carboxyl-terminal amino acid of chain, to promote attachment of the amino acid to the matrix M) are transferred from the selected reservoir, for example, from reservoir 16a, to the vessel 12.

For this second transfer, (and for any subsequent transfers), the vessel 12 is first turned upside-down so that the gaseous portion of chamber 56 communicates with the port 52a. Then, the vessel 12 is vented to atmospheric pressure to exhaust any increased vapor pressure caused by mixing of the contents of vessel 12. Venting of the vessel 12 occurs through the exhaust system 22, as described below.

The vessel 12 is then equilibrated to the reference pressure P, and a second volume of gas is removed from the vessel 12, by operating the valves 66 and 72 and withdrawing the syringe plunger 74b to the desired displacement volume. Valve 72 is deactuated and the valve 44a is actuated, connecting the selected reservoir 16a to the vessel 12. The pressure differential between the reservoir and the vessel transfers the reagent Ra (a volume proportional to the volume of gas removed from the vessel) from the reservoir 16a to the vessel 12. Then, valve 44a is deactuated, the line 20 is flushed with nitrogen as described previously, and the vessel 12 is shaken for a short time to mix its liquid and solid contents.

Following the above procedure, any further solvents or reagents that may be required for the reaction are added to the vessel 12. Then, the reaction is allowed to proceed by slowly reciprocating the vessel 12 by the shaker 62. After a prescribed period of time for the reaction to occur, the skaker 62 is turned off and the vessel 12 is turned right-side-up so that the liquid portion of the vessel 12 communicates with the port 52a. In this position, the liquid and gaseous contents of the vessel 12 are emptied to the exhaust system 22 by application of a vacuum.

More specifically, the exhaust system 22 broadly comprises a vacuum pump 84, a cold trap 86, and a waste collection receptacle 88. The system 22 connects to the rest of the system 10 at the valve 82, through a line 90 and a connecting valve 92. The valve 92, in its deactuated connection, isolates the exhaust system 22 from the rest of the system 10. When actuated, the valve 92 connects the rest of system 10 to the waste receptacle 88 through a line 94.

The first step for the removal of liquid contents of the vessel 12, is to actuate a valve 96, closing the waste collection receptacle 88 to the atmosphere. Then, the vacuum pump 84 is turned on, and the receptacle 88 is evacuated through a connnecting line 102. A bleed/check valve 104, positioned in the line 102, allows only a prescribed level of vacuum in the receptacle 88, as well as parts of the system 10 connected thereto, to prevent damage by excessive vacuum to the vessel 12, and the connecting valves and lines. The bleed/check valve 104 also holds the vacuum in the exhaust system when the pump 84 is turned off.

After the receptacle 88 is evacuated, the vacuum pump 84 is turned off and the valves 92 and 82 are actuated. Thus, the vessel 12 and the receptacle 88 communicate through line 68, actuated valve 82, line 90, actuated valve 92, and line 94. The difference in pressure between the receptacle 88 and the vessel 12 causes the liquid contents of the vessel 12 to be transferred to the receptacle 88. Because the vacuum pump is turned off while the liquid contents are being transferred, volatiles that are drawn off into the receptacle 88 are not drawn into the vacuum pump 84. After emptying the reaction vessel 12, the valve 92 is then deactuated, cutting off the exhaust system 22 from the vessel 12.

Then, valves 80 and 66 are actuated so that the vessel 12 is repressurized to the reference pressure P, and any liquid remaining in the valve 66 is pushed into the vessel 12. After repressurization of the vessel, valves 80 and 66 are again deactuated, and the valve 92 is actuated to connect the the vessel 12 with the exhaust system 22, and the vessel is evacuated for a second time, as described above. This second pressurization and evacuation of the vessel 12 completely and effectively empties the liquid and gaseous contents of the vessel 12. The valve 92 is then deactuated, closing the exhaust system 22 to the system 10, and the vessel 12.

Waste collected in the receptacle 88 is removed by deactuating the valve 96. The deactuated valve 96 forms dual connections. Waste in the receptacle 88 is removed through a line 98 and one of the deactuated valve 96 connections. At this time the receptacle 88 is vented to the atmosphere through a line 100 and the other of the deactuated valve 96 connections.

Thus, any desired combination of reactants (amino acids, solvents, reagents) are easily transferred from the reservoirs to the reaction vessel 12, and the transfer is automatically controlled by the processor 24, by regulating the valves, and the stroke of the volume displacement pump 18. The entire peptide synthesis is processor-controlled by also controlling the vacuum pump in the exhaust system, the shaker 62, and the remaining valves in the system.

A user of the system needs only to enter a desired peptide sequence into the processor 24. Under control of a suitable program, the processor then automatically selects pre-determined appropriate reaction conditions (time, duration, amino acid, solvent or reagent) for each amino acid addition to the peptide, and initiates the appropriate commands, in the appropriate sequence, and at the appropriate times, to obtain these conditions.

The exhaust system 22 also serves to clean the main transfer line 20 by evacuation. For this function, the valves 80 and 92 are actuated, and the vacuum pump 84 is turned on. Thus, the line 20 communicates with the vacuum pump 84 through the deactuated valve 66, the line 70, the deactuated valve 82, the line 90, the actuated valve 92 and the line 94, and the receptacle 88. Liquid remaining in the line 20 is thus collected in the receptacle 88.

Also, as described above, excess pressure can result in the reaction vessel 12 due to the vapor pressure of volatile solvents, and the shaking of the vessel. It can also result from gaseous by-products of some of the reactions required for peptide synthesis. This excess pressure is removed from the vessel 12, by venting it to the atmosphere through the exhaust system 22. Venting is accomplished by deactuating the valve 96, and actuating the valves 92 and 82 while the vacuum pump 94 is turned off. Thus the vessel 12 communicates the atmosphere through the receptacle 88 and the valve 96. Subsequent repressurization of the vessel to the reference pressure thus allows for exact metering of reagent transfer.

Furthermore, the quantity of reactant transferred from a reservoir to the vessel can be varied easily from transfer to transfer by varying the stroke of the volume displacement pump 18 and thereby changing the volume of gas withdrawn from the reaction vessel 12. Moreover, if the volume to be withdrawn exceeds the capacity of the pump 18 in single-stroke displacement of the plunger 74b, multiple strokes can be used to obtain the desired volume.

Specifically, after the first stroke, the valve 78 is actuated to keep the vacuum in the system and to vent the interior of the pump 18 and the plunger 74b is returned to its zero-volume position. Then, the valve 78 is deactuated and the plunger is withdrawn again. This procedure is repeated as often as is necessary to withdraw the desired volume from the vessel 12. Thus, using multiple strokes of the pump, a single syringe of small volume, can be used to withdraw large volumes. Also, the same syringe can be used to withdraw both large and small volumes at will.

To refill or replace one of the reservoirs 14a–14n, a valve 106, positioned in the line 30c, is actuated. The valve 106 controls nitrogen flow from the pressure source 26 to manifold 38. When the valve 106 is actuated, the manifold 38 is cut off from the pressure source 26, and pressure in the manifold 38 is vented to the atmosphere. Then, the selected reservoir 14a–14n may be removed for filling or replacement.

Similarly, a valve 108 is positioned in line 30b, for refilling or replacing the reservoirs 16a–16n. After the valve 108 is actuted, the corresponding valve 36a–36n is actuated, thus venting the selected reservoir 16a–16n to the atmosphere, so that it may be removed for filling or replacement.

As stated above, cross-contamination between amino acids must be avoided if a peptide chain having the appropriate sequence is to be built. For this reason, the reagent reservoirs 16a–16n are connected upstream from the amino acid reservoirs 14a–14n along the common transfer line 20. Thus when reagents and/or solvents are transferred to the vessel after the selected amino acid is transferred, any residual amino acid remaining in the main line 20 is flushed into the vessel by flow of the solvents and/or reagents through the line 20.

The pressure in the system 10 remains constant even when solvents of varying vapor pressure are used. This is because the regulator 28 regulates total system pressure, which includes vapor pressure as well as a component from the pressure source 26. An accurate delivery of solvents, reagents and amino acids can thus be assured because the system is maintained at the constant reference pressure.

The system 10 is preferably equipped with a yield monitor, indicated generally at 120, to assess the completeness of each amino acid addition. The yield may be assessed by the use of a covalent reversible monitoring agent which binds reversibly to the free amino termini of those peptide chains that did not react with the last preceding amino acid added to the peptide chains.

A monitoring method using such an agent proceeds as follows. After each addition of a blocked amino acid to the anchored peptide chains, but before deblocking to receive the next amino acid to be added to the peptide chain, the matrix M containing the anchored peptide chains is reacted with the monitoring agent. The contents of the vessel are then thoroughly washed, and the monitoring agent is selectively removed from those peptide chains to which it is attached, under conditions that leave intact the blocked ends of the peptide chains that reacted with the last preceding amino acid, and which leave intact the peptide chains themselves. The cleaved monitoring agent is then transferred to a sample cell 122 in a monitor 120, where the concentration of the monitoring agent is measured.

More specifically, the monitor 120 connects to the rest of the system 10 through the valve 92. Valve 92 in its deactuated, or normal connection, places the monitor 120 in communication with the valve 82. To effect the transfer to the sample cell 122, the valve 82 is actuated, thereby connecting the vessel 12 to the cell 122 by way of valve 66, line 68, and valve 92. The transfer is driven by a pressure differential between the sample cell 122, which is at atmospheric pressure, and the vessel 12, which is at the system pressure P. A detector 124, such as a spectrophotometer which senses the absorbance of the contents of the cell 122, thereby measures the concentration of the monitoring agent therein. The amount of monitoring agent is thus quantitated and the yield in the previous amino-acid addition step determined by the processor 24, which compares this value to the desired yield. This yield corresponds directly to the number of free unreacted amino termini on the anchored peptide chains, and thus is representative of the portion of the peptide chains that did not react in the last preceding amino acid addition. If the yield is not high enough, the previous amino acid addition may be repeated until the desired yield is attained. If successive repetitions do not improve the yield, the entire synthesis may be terminated, or a second blocking group, called a capping agent, may be added to permanently block the unreacted amino termini of these peptide chains, and prevent further additions to them. Thus it is easier to separate these shorter peptide chains from the peptide chains of interest than to separate the peptide chains differing by only one amino acid residue from the peptide chains of interest.

The covalent-and-reversible monitoring reagents we use are a class of trityl (triphenylmethyl) -based compounds having trityl-based groups, such as trityl, monomethoxytrityl, dimethoxytrityl, and trimethoxytrityl as the active monitoring agent of the compound. These trityl-based groups may be generated from trityl-based compounds such as trityl-based halides (e.g. chloride, bromide), trityl-based carboxylates (e.g. acetate, trifluoroacetate), or trityl-based acid anions. Also, these compounds have high extinction coefficients which make monitoring very sensitive. The presence of the monitoring agent is easily detected by absorbance in a spectrophotometer at the appropriate wavelength, thus making monitoring simple and economical.

Under certain monitoring conditions, such as those described below, these trityl-based compounds are specific for free amino groups and do not react with side groups of blocked amino acids. Hence, the background noise of the monitoring is very low, and remains low even as the peptide chain length increases. The trityl-based compounds described and used herein as monitoring reagents are representative of a wide range of chemical reactivity. It has been reported that mono-, di- and trimethoxytrityl chlorides show regularly increasing reactivity, with each methoxy group increasing the reaction rate approximately ten fold (*J. Amer. Chem. Soc.* 84: 430 (1962) and 85: 3821 (1963)). These methoxytrityl compounds can be detected spectrophotometrically at visible light wavelengths, which makes detection simple and inexpensive. Also, the trityl moieties of these monitoring agents have molar extinction coefficients on the order of $10^5$, which make them very sensitive.

A monitoring method utilyzing these trityl-based compounds proceeds as follows:

(A) REACT THE SOLID PHASE WITH A TRITYL-BASED COMPOUND

At the end of each addition of blocked amino acid to a peptide chain anchored to a solid phase, the solid phase is reacted with an excess of a trityl-based compound that forms a covalent bond with amino groups in a reaction solution and under reaction conditions that promote such covalent bonding.

(B) WASH THE SOLID PHASE TO REMOVE NON-SPECIFICALLY ADSORBED TRITYL-BASED GROUPS FROM THE SOLID PHASE

After the reaction of step (A), the reaction solution is removed from the solid phase and the solid phase is washed with a washing solution to remove trityl-based compound that is non-covalently and non-specifically bound to the solid phase.

(C) REMOVE SPECIFICALLY-BOUND TRITYL-BASED GROUPS FROM THE SOLID PHASE

After washing, trityl-based groups remaining on the solid phase are specifically bound to the amino termini of the peptide chains anchored to the matrix M of solid phase. These trityl-based groups are cleaved from these amino termini with a cleaving reagent that selectively removes the covalently bonded trityl-based groups from the amino groups. The cleaving reagent does not remove the BOC amino-terminal blocking group or other blocking groups used to protect sensitive side groups of certain amino acids. The trityl-based groups are soluble in the cleaving reagent, which comprises the liquid phase.

(D) QUANTITATE THE AMOUNT OF SOLUBLE TRITYL-BASED GROUPS

The amount of trityl-based groups soluble in the liquid phase are quantitated.

A specific reaction protocol for a monitor utilizing dimethoxytrityl (DMT) as a representative monitoring agent proceeds as follows:

(A) REACT THE SOLID PHASE WITH AN EXCESS OF DIMETHOXYTRITYL CHLORIDE

At the end of each addition of a blocked amino acid, but before deblocking, the solid phase matrix M in the vessel 12 is washed twice with dichloromethane (DCM). A freshly-prepared reaction solution containing dimethoxytrityl chloride (DMT-Cl) (approximately 15-30 ml solution per gram of solid phase resin) is added to the vessel 12. This reaction solution is prepared using three volumes of a first solution comprising 2.85 mg/ml DMT-Cl in dichloroethane (DCE), and one volume of a second solution comprising 44.8 mM diisopropylethylamine (DIEA) in DCM.

The reaction solution and solid phase are mixed for one minute at room temperature. During this time and under these conditions, the dimethoxytrityl (DMT) group reacts stoichiometrically with free amino groups which may be present. These free amino groups are found at the termini of any peptide chain that did not react with the last preceding amino acid.

(B) WASH THE SOLID PHASE TO REMOVE NON-SPECIFICALLY ADSORBED DIMETHOXYTRITYL GROUPS FROM THE SOLID PHASE

The contents of the vessel 12 are then washed with six, one-minute washes at room temperature to remove excess DMT-Cl and DMT-Cl that is non-specifically adsorbed to the peptide or to the solid support matrix. The washes are performed using a washing solution comprising 1 mM hydroxybenzotriazole (HOBT) and 1% trifluoroethanol (TFE) in DCE. The washing solution is prepared using a 100-fold concentrated stock solution of 100 mM HOBT in TFE and diluting it 1:100 (V/V) in DCE.

(C) REMOVE SPECIFICALLY BOUND DIMETHOXYTRITYL GROUPS FROM THE SOLID PHASE

After washing, the remaining DMT groups that are specificaly bound to the amino termini of the peptide chains anchored to the matrix M are cleaved from these amino termini by adding a cleaving solution to the solid phase and allowing it to react for one minute with gentle mixing. The cleaving solution comprises 3% trichloroacetic acid (TCA) (W/V) in a DCE-anisole solution that is 10% anisole by volume. The DMT groups removed from the solid phase under these conditions are soluble in the cleaving solution (which comprises the liquid phase). The anisole is present as a scavenger for carbonium ions. Under the acidic conditions caused by the cleaving solution, DMT-Cl may form DMT-carbonium ions, which are highly reactive and may interact with the various amino acid residues of the peptide chains. This reaction is irreversible and, if it is allowed to proceed, it would undesirably modify the growing peptide chain. Anisole binds to DMT-carbonium ions and prevents their formation.

(D) QUANTITATE THE AMOUNT OF SOLUBLE DIMETHOXYTRITYL GROUPS

The liquid phase is then transferred to the monitor 120, and the absorbance of DMT at 500 nm is measured by the detector 124. The quantity (in umoles) of DMT is then calculated using this absorbance value, the extinction coefficient, and the volume of the liquid phase. The molar extinction coefficient for DMT in the cleaving solution has been determined to be $7.9 \times 10^4$ L $M^{-1} cm^{-1} + 3000$.

A specific reaction protocol using monomethoxytrityl chloride as a monitoring reagent follows the protocol described above for monitoring with DMT-Cl, with the excetion that monomethoxytrityl chloride is substituted for DMT-Cl and the reaction time in step (A) of the DMT-Cl monitoring protocol is increased to seven minutes. Also, the amount of monomethoxytrityl groups in the cleaving solution is determined by absorbance at 475 nm using an extinction coefficient of $5.7 \times 10^4$ L $M^{-1} cm^{-1}$.

Similarly, a specific reaction protocol using trimethoxytrityl chloride follows the above reaction protocol for DMT-Cl with the exception that trimethoxytrityl chloride is substituted for DMT-Cl and the washing solution of step (B) of the DMT-Cl monitoring protocol is changed to methylene chloride. The amount of trimethoxytrityl groups in the cleaving solution is determined by absorbance at 480 nm using an extinction coefficient of $1.1 \times 10^5$ L $M^{-1} cm^{-1}$.

Another reaction protocol using trityl chloride as a representative monitoring reagent proceeds as follows.

(A) REACT THE SOLID PHASE WITH AN EXCESS OF TRITYL CHLORIDE

At the end of each addition of a blocked amino acid, but before deblocking, the contents of the vessel 12 are washed twice with dimethylformamide (DMF). Then, a solution of 5% trityl chloride and 5% DIEA in DMF is added to the vessel 12 and the contents are mixed for 15 minutes at room temperature.

(B) WASH THE SOLID PHASE TO REMOVE NON-SPECIFICALLY ADSORBED TRITYL GROUPS FROM THE SOLID PHASE

The contents of the vessel 12 are then washed twice with DMF to remove any excess, unreacted trityl chloride. All trityl groups left in the vessel 12 are thus bound to the free amino groups on the matrix M.

(C) REMOVE SPECIFICALLY-BOUND TRITYL GROUPS FROM THE SOLID PHASE

Specifically, they are bound to the termini of the peptide chains that did not react with the last preceding amino acid. The trityl groups bound to the matrix M in the vessel are then removed by adding a solution of 7% TCA in DCM to the solid phase and allowing it to react for 10 minutes with gentle mixing. Under these conditions, the trityl-amino bond is broken, forming soluble trityl carbonium ions.

(D) QUANTITATE THE AMOUNT OF SOLUBLE TRITYL GROUPS

The liquid phase is then transferred to the monitor as described previously, and the level of the trityl carbonium ions is quantitated by measuring the absorbance at 259 nanometers. In the above TCA-DCM solvent, the trityl moiety has a molar extinction coefficient on the order of $10^3$. Thus, the yield at each amino acid addition step in the reaction vessel 12 can be determined with a high degree of accuracy and without significantly destroying the peptide chains that were synthesized correctly.

Numerous experiments have been performed to optimize the monitoring protocols described above and to demonstrate their effectiveness. The experiments described below have been performed using DMT-C1 as a representative monitoring reagent. Similar experiments have been performed for the monitoring reagents described above.

Experiment No. 1. Determination of the Molar Extinction Coefficient of DMT-C1 Monitoring Reagent in the Cleaving Solution The molar extinction coefficient of DMT-C1 in the cleaving solution was determined for each of eight separate samples of known DMT-C1 concentration. Each sample was prepared by weighing out an exact quantity of DMT-C1 (weighing around 5.0 mg), and dissolving it in one milliliter of cleaving solution. Each sample was then diluted 1:2000 in the cleaving solution and the absorbance at 500 nm was measured in a Bausch and Lomb spectrophotometer. Using a molecular weight of 338.8 g/mole for DMT-C1, an extinction coefficient was calculated for each sample from the measured absorbance. The results are shown in Table 1. The average molar extinction coefficient for DMT-C1 in cleaving solution was calculated to be $7.9 \times 10^4$ L $M^{-1}cm^{-1} \pm 3000$.

TABLE 1

| | | DETERMINATION OF EXTINCTION COEFFICIENT | | | |
|---|---|---|---|---|---|
| TRIAL | # mg/ml | DILU-TION | CONCEN-TRATION | $A_{500}$ | EXTINCTION COEFFICIENT |
| 1 | 4.9 | 1:2000 | 7.23 uM | 0.59 | $8.16 \times 10^4$ |
| 2 | 5.1 | 1:2000 | 7.53 | 0.60 | $7.97 \times 10^4$ |
| 3 | 6.1 | 1:2000 | 9.00 | 0.725 | $8.06 \times 10^4$ |
| 4 | 5.7 | 1:2000 | 8.41 | 0.642 | $7.63 \times 10^4$ |
| 5 | 5.4 | 1:2000 | 7.97 | 0.609 | $7.64 \times 10^4$ |

EXTINCTION COEFFICIENT (average) = $7.9 \times 10^4$ ($\pm 3000$)
M.W. = 338.8 g/mole The effect of 10% anisole on the absorbance of DMT-C1 at 500 nm was determined as follows. A DMT-C1 stock solution was prepared in a solution of 3% TCA in DCE (cleaving solution without anisole). Five DMT-C1 samples of varying concentration were prepared by diluting the DMT-C1 stock in 3% TCA in DCE. For each sample, the absorbance at 500 nm was measured in a Bausch and Lomb spectrophotometer. Then each sample was made 10% by volume in anisole, and the absorbance at 500 nm was again measured. This absorbance value was corrected for the increase in volume caused by the addition of the anisole. The absorbance values for each sample with anisole ( ▲ ) and without anisole ( ● ) are plotted against their concentration, and the resulting graph is shown in FIG. 3. The absorbance values were found to be virtually identical for each sample with and without anisole. Also, the absorbance at 500 nm increased linearly with concentration of DMT-C1 in cleaving solution, whether anisole was present or absent. Thus, the components of the cleaving solution (TCA, DCE and anisole) do not show any adverse affects on the absorbance measurements of the DMT groups in solution.

Experiment No. 2A. Effect of Cleaving Solution on the Amino-Blocking Group (BOC)

The effects of the cleaving solution on the amino-blocking group were determined by incubating eight samples with cleaving solution at room temperature for time intervals ranging from 2 minutes to 30 minutes. Each sample contained approximately equal quantities (4.6–4.7 mg per sample) of a solid phase test resin having an amino-blocked amino acid attached thereto. The test resin used in this experiment is a BOC-leucine resin (0.83 meq/gm), which is available commercially. The test resin is represents a solid phase having a peptide chain anchored to it. After incubation, the cleaving solution was removed and the solid phase was tested for the presence of free amino groups using ninhydrin—a standard test for amines. As shown in Table 2A, no positive ninhydrin reactions were observed on the solid phase, even when it was incubated with cleaving solution for 30 minutes. These results demonstrate that the cleaving solution, which is used to remove DMT monitoring agent bound to free amino groups, does not remove the BOC amino-blocking group (also bound to amino groups), especially under the reaction conditions employed in the monitoring protocol for DMT-C1, described above.

TABLE 2A

| EFFECT OF CLEAVING SOLUTION ON BOC GROUP | | | |
|---|---|---|---|
| TUBE # | # MG RESIN* | TIME (min) | NINHYDRIN |
| 1 | 4.6 | 2 | — |
| 2 | 4.6 | 4 | — |
| 3 | 4.6 | 6 | — |
| 4 | 4.7 | 8 | — |
| 5 | 4.6 | 10 | — |
| 6 | 4.7 | 12 | — |
| 7 | 4.6 | 20 | — |
| 8 | 4.6 | 30 | — |

*BOC-Leu resin @ 0.83 meg/gm

Experiment No. 2B. Effect of the Washing Solution on DMT Monitoring Agent Covalently Bound to the Amino Groups on a Solid Phase The effect of the washing solution (1 mM HOBT and 1% TFE in DCE) on DMT specifically bound to the amino groups on the amino termini of anchored peptide chains was determined as follows. A test resin comprising a DMT-blocked amino acid attached thereto was prepared starting with a BOC-leucine resin (as described in Experiment No. 2A), removing the BOC blocking group, and incubating the unblocked amino acid resin according to the reaction protocol for DMT-C1. The resulting DMT-leucine test resin was used to prepare four samples, each containing approximately 0.1 mg solid phase resin per sample (0.83 meq/gm). The samples were incubated with excess washing solution for time periods ranging from 15–40 minutes, as identified in Table 2B. The washing solution was removed from the solid phase, and the solid phase was tested for the presence of free amine groups by the standard ninhydrin test. The results, shown in Table 2B, indicate slightly-positive ninhydrin reactions for the samples incubated for 24 and 40 minute time periods. These results demonstate that, while some DMT is cleaved from DMT-bound Leu-resin under the longer incubation time periods (24 and 40 minutes), DMT is not removed at any detectable level when the washing conditions described above for monitoring with DMT-Cl are employed (a total of six one minute washes).

TABLE 2B

EFFECT OF WASHING SOLUTION ON DMT-BLOCKED AMINE

| TUBE # | # MG RESIN* | TIME (min) | NINHYDRIN |
|---|---|---|---|
| 1 | 0.1 | 15 | — |
| 2 | 0.1 | 18 | — |
| 3 | 0.1 | 24 | + (slight) |
| 4 | 0.1 | 40 | + (slight) |

*DMT-Leu-resin @ 0.83 meg/gm

Experiment No. 2C. Effect of the Washing Solution on the amino-blocking (BOC) groups The effect of the washing solution (1 mM HOBT and 1% TFE in DCE) on the amino-blocking (BOC) group was also determined using a method similar to that described for Experiment No. 2A. Three separate samples, each comprising a solid phase test resin of BOC-Leu resin (approximately 0.1 mg each) were incubated with washing solution for 30, 60 and 90 minutes at room temperature. After incubation, the washing solution was removed and the solid phase was monitored for free amino groups using the standard ninhydrin test. As seen in Table 2C, the solid phase exhibited no ninhydrin-positive reactions for any of the time periods. These results show that the washing solution does not remove the amino-blocking (BOC) group, especially under the washing conditions described for monitoring with DMT-Cl (a total of six minutes).

TABLE 2C

EFFECT OF WASHING SOLUTION ON AMINO-BLOCKING GROUPS

| TUBE # | # MG RESIN* | TIME (min) | NINHYDRIN |
|---|---|---|---|
| 1 | 0.1 | 30 | — |
| 2 | 0.1 | 60 | — |
| 3 | 0.1 | 90 | — |

*BOC-Leu resin @ 0.83 meg/gm

Experiment No. 3. Effect of DMT Monitoring on the Number of Moles of Amine that Remain Linked to the Peptide Chains.

This experiment was performed to demonstrate that monitoring with DMT-Cl during peptide synthesis is completely reversible and does not have a destructive effect on the peptide chains anchored to the solid phase resin. Two parallel reaction vessels, each containing a solid phase of 200 mg BOC-Leu resin were subjected to a series of three consecutive amino acid couplings with BOC-Leu as the amino acid. Each coupling involves the steps of (1) DEBLOCKING: removing the BOC blocking group from the amino termini of the anchored peptide chains by incubating with trifluoroacetic acid (TFA) and neutralizing with DIEA:

(2) NINHYDRIN TESTING: removing an aliquot of the solid phase and testing it with the standard ninhydrin test to quantitate the amount of free amine present; and (3) ADDING A NEW BLOCKED AMINO ACID: adding BOC-leucine to the unblocked termini of the anchored peptide chains using dicyclohexylcarbodiimide and washing the solid phase resin to remove non-specifically bound BOC-leucine.

In addition to the above coupling steps, one of the two reaction vessels also included monitoring the resin with DMT-Cl after steps (1) and (3) above. The other vessel was not monitored. The monitoring of the resin after step (3) is a routine procedure that occurs after each coupling to determine the completeness of the reaction. Monitoring the unblocked resin after step (1) is not a routine procedure. This procedure has been included to determine whether DMT-Cl irreversibly binds to unblocked amino termini.

The results of the ninhydrin test on the solid phase before and during the three consecutive couplings are shown in Table 3. The results show equivalent amounts of free amine present on unblocked resin from the monitored and unmonitored vessels. Therefore, DMT-Cl does not irreversibly react with free amino groups and DMT-Cl monitoring has no effect on the peptide synthesis reaction.

TABLE 3

EFFECT OF DMT MONITORING ON UMOLES AMINE

| MONI-TORED | # OF COU-PLINGS | # MG RESIN | DILU-TION | $A_{570}$ | # uMOLES AMINE (exp) |
|---|---|---|---|---|---|
| no | 0 | 5.5 | 1:250 | 0.181 | 1.20 |
| yes | 0 | 5.4 | 1:250 | 0.190 | 1.27 |
| no | 1 | 4.7 | 1:250 | 0.250 | 1.67 |
| yes | 1 | 4.8 | 1:250 | 0.260 | 1.73 |
| no | 2 | 5.4 | 1:250 | 0.273 | 1.82 |
| yes | 2 | 5.5 | 1:250 | 0.270 | 1.80 |
| no | 3 | 4.3 | 1:250 | 0.209 | 1.39 |
| yes | 3 | 4.3 | 1:250 | 0.221 | 1.47 |

Experiment No. 4. Reproducibility of Monitoring

The reproducibility of the DMT-Cl monitoring reaction was determined by successive and repeated monitoring of partially reacted resins. Two partially-reacted resins (1.25% free amino groups and 2.35% free amino groups) were prepared using Bpoc-blocked amino acids, according to the method described in "Quantitative Monitoring of Solid-Phase Peptide Synthesis by the Ninhydrin Reaction", Virender K. Sarin, Stephen B. H. Kent, James P. Tam, and R. B. Merrifield, Analytical Biochemistry 117: 147–157 (1981). Each batch of resin was repeatedly monitored with DMT-Cl according to the monitoring protocol described above, and the amount of DMT in the liquid phase was determined by measuring the absorbance at 500 nm. The quantity of DMT-Cl (in umoles) was calculated from this absorbance value, the volume of the liquid phase and the extinction coefficient of DMT-Cl. Because DMT reacts stoichiometrically with free amine groups, the moles of DMT is equivalent to the moles of free amine present on the resin. The % free amine is then calculated from the moles of free amine and the known amount of total amine on the starting resin (calculated from the meq/gm resin). The % free amine remaining on the 1.5% free amine resin after successive monitoring reactions are shown in Table 4A. Similarly, the % free amine remaining on the 2.35% free amine resin after sucessive monitoring reactions are shown in Table 4B. These results show an average % free amine to be 1.27% ± 0.06 for the 1.25% resin and 2.34% ± 0.09 for the 2.35% resin. Also, the % free amine did not decrease with successive trials. These results demonstrate the high reproducibility and the lack of any irreversible binding by the DMT-Cl monitoring reagent.

TABLE 4A
REPRODUCIBILITY OF MONITORING

| TRIAL # | A500 | VOLUME | DILUTION | % FREE AMINE |
|---------|------|--------|----------|--------------|
| 1 | 0.54 | 29.3 | 1:10 | 1.21 |
| 2 | 0.59 | 29.0 | 1:10 | 1.30 |
| 3 | 0.6 | 28.9 | 1:10 | 1.32 |
| 4 | 0.61 | 28.5 | 1:10 | 1.32 |
| 5 | 0.56 | 28.5 | 1:10 | 1.22 |
| 6 | 0.579 | 28.5 | 1:10 | 1.26 |
| 7 | 0.58 | 28.9 | 1:10 | 1.28 |

% Free Amine (average) = 1.27% (±0.6)
Volume collected (average) = 28.8 ml (±0.5)
$E_{500} = 7.9 \times 10^4 \, L \, M^{-1} \, cm^{-1}$

TABLE 4B
REPRODUCIBILITY OF MONITORING

| TRIAL # | A500 | VOLUME | DILUTION | % FREE AMINE |
|---------|------|--------|----------|--------------|
| 1 | 0.295 | 26.9 | 1:40 | 2.42 |
| 2 | 0.27 | 27.1 | 1:40 | 2.24 |
| 3 | 0.282 | 27.1 | 1:40 | 2.33 |
| 4 | 0.287 | 27.0 | 1:40 | 2.36 |
| 5 | 0.29 | 26.5 | 1:40 | 2.34 |

% Free Amine (average) = 2.34% ± 0.9%
Volume collected (average) = 26.9 ml ± 0.4
$E_{500} = 7.9 \times 10^4 \, L \, M^{-1} \, cm^{-1}$ Experiment No. 5. Effect of the Washing Procedure on the Removal of DMT and DMT-CL from the Solid Phase Resin The effectiveness of the washing steps taken in step (B) of the DMT-C1 monitoring protocol in removing non-specifially bound DMT-C1 from the solid phase resin were analyzed as follows. The 1.25% and 2.35% partially-reacted resins, prepared as described for Experiment No. 4 above, were reacted with DMT-C1 monitoring reagent according to the monitoring protocol described above for DMT-C1, with the exception that the number of one-minute washes in step (B) of the protocol was varied to three-, four-, five-, six-, eight- and fourteen-one minute washes. The amount of DMT (in umoles) remaining attached to the resin after each of these washes was determined by removing the DMT from solid phase and quantitating the amount of DMT, according to steps (C) and (D) of the monitoring protocol. The % free amine was calculated (as described in Experiment No. 4) from the amount DMT. This value was plotted against the number of washes, and the results are depicted in FIG. 2A for 1.25% partially-reacted resin and in FIG. 2B and for 2.35% partially-reacted resin. These graphs show a two-phase removal of DMT from the resin. The shallow curve (between 6 and 14 washes) demonstrates slow removal of DMT on the resin, which is likely to represent partial hydrolysis of the DMT-amino terminal bond. The steeper curve (up to six washes) demonstrates fast removal of DMT-C1 from the resin, and this curve is likely to represent removal of DMT-C1 that is non-specifically adsorbed to the resin. From the results of the washing curves, six one minute washes were chosen as the optimal conditions for removing non-specifically adsorbed DMT without hydrolyzing specifically bound DMT.

Experiment No. 6. Interactions of DMT-C1 Monitoring Reagent with Various Amino Acids Any desired interactions of the DMT-C1 monitoring reagent with the various amino acids was determined by exposing test resins, each resin having a different blocked-amino acid attached thereto, to the DMT-C1 monitoring protocol described above. Theoretically, the amount of DMT-C1 adsorbed to each resin should be zero, because the BOC group is blocking any reactive amino groups. However, because of the varied structures of the amino acids, some of which require special blocking groups to protect reactive portions of the amino acid, the lack of undesired interactions must be demonstrated experimentally.

Various test resins, identified in Table 5, each having a different blocked amino acid attached to it, were monitored with the DMT-C1 monitoring protocol described above, and the amount of DMT bound to the resin was determined from the amount of soluble DMT groups (in umoles), according to step (D) of the DMT-C1 monitoring protocol. The % free amine was calculated using an amount of amine equivalent to the amount of DMT groups, divided by the the known amount of total amine on the resin. These calculations are described more fully in Experiment No. 4. The results, depicted in Table 5, show that, while some of the protected forms of histidine and arginine exhibit high background color, at least one form of each of the common amino acids demonstrates minimal background color. When preparing peptides containing arginine and histine, only those protected amino acids showing low background will be chosen to prepare those peptides. These results demonstrate that the background noise of monitoring with DMT-C1 is now for each amino acid, and will therefore, remain low even as the peptide chain length increases.

TABLE 5
BACKGROUND COLOR FROM VARIOUS RESINS

| AMINO ACID RESIN | # mg | A500 | % OF TOTAL AMINE |
|------------------|------|------|------------------|
| ASN | 38.6 | 0.003 | * |
| GLN | 61.4 | 0.005 | * |
| LYS(C1Z) | 68 | 0.15 | 0.1 |
| ALA | 65 | 0.075 | * |
| PRO | 66 | 0.075 | * |
| GLY | 65 | 0.085 | * |
| ILE | 66 | 0.102 | 0.1 |
| SER(Bzl) | 65 | 0.16 | 0.1 |
| CYS(MeBzl) | 62 | 0.15 | 0.06 |
| GLU(Bzl) | 64 | 0.095 | 0.1 |
| Phe | 62 | 0.06 | * |
| TYR | 59 | 0.101 | 0.1 |
| CYS(Bzl) | 56 | 0.096 | 0.1 |
| ASP(Bzl) | 60 | 0.152 | 0.1 |
| VAL | 62 | 0.199 | 0.2 |
| THR(Bzl)-LEU | 32.8 | 0.17 | 0.1 |
| TRP-LEU | 32 | 0.185 | 0.1 |
| ASN(XAN)-LEU | 31.9 | 0.135 | 0.1 |
| NORLEU | 43.3 | 0.126 | 0.1 |
| MET | 58 | 0.3 | 0.3 |
| ARG(TOS) | 90 | 1.64 | 0.8 |
| ARG(NO$_2$) | 56.1 | 0.02 | * |
| HIS(Bzl)-LEU | 15.3 | 0.004 | * |
| HIS(TOS)-LEU | 33.8 | 3.8 | 2 |
| HIS(BOM)-LEU | 80 | 70.5 | 31 |

*less than 0.05%

In summary, these representative experiments demonstrate that monitoring peptide synthesis with DMT-C1 is a sensitive and specific method for determining the amount of free amino groups after each amino acid coupling reaction. The monitoring method is reproducible and quantitative, and it is non-destructive of the growing peptide chains.

Thus, we have provided an improved system for synthesizing peptides wherein the transfers of amino acids, reagents and solvents from their respective reservoirs to the reaction vessel are accomplished quickly, easily, and economically by volume displacement and pressure equilibrium. Cross-contamination of reagents in the transfer lines and valves is minimal. The system can be easily optimized for producing a high yield at each amino acid addition step, and the yield at each step can be monitored easily and effectively with a yield monitor to facilitate the production of peptides having a high ultimate yield.

We have also demonstrated an improved method and apparatus for quantitating free amino groups. The method utilyzes a class of trityl-based compounds as monitoring reagents whose active monitoring agents are the tritylbased groups derived from these compounds. These agents covalently and reversibly bind to free amino groups under certain reaction conditions, and it is this reversible binding that provides the means for assaying amino groups. The method and apparatus disclosed is especially suited to monitoring the solid-phase synthesis of peptides, wherein the completeness of each amino acid coupling reaction can be monitored by directly quantitating the amount of unreacted, or free amino groups.

It will thus be seen that the objects set forth above, among those made apparent from the preceding description, are efficiently attained. Also, certain changes may be made in carrying out the above methods and in the above constructions without departing from the scope of the invention.

For example, the reference pressure may be momentarily increased when the vessel 12 is to be flushed, for faster removal of waste and washes. Also, the monitor 120 may be adapted to accomodate other monitoring methods or other monitoring agents having similar reactivity with free amines.

Also, the monitor and the monitoring method could be used in connection with apparatus other than peptide synthesizing apparatus to detect the presence of free amine groups. For example, when the composition of a peptide is analyzed, the peptide is hydrolyzed into its amino acid subunits, each amino acid subunit is isolated by chromatography separation, and the quantity of each subunit is determined. This quantitation can be made using the trityl-based monitoring agents and the monitoring methods described herein, because these agents bind covalently and reversibly to free amino groups under certain reaction conditions, thus providing a selection mechanisn to assay the amount of free amino groups.

Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A process for monitoring a solid-phase peptide synthesis for free amino ends of unreacted peptide chains, comprising:
   A. synthesizing a peptide chain by adding a blocked amino acid, comprising an amino acid bound to a blocking agent, to a peptide chain that is anchored to the solid-phase;
   B. reacting the solid phase with a monitoring agent that forms a covalent bond with amino groups under reaction conditions that promote such covalent bonding.
   C. washing the solid phase with a washing solution to remove non-covalently bound monitoring agent from the solid phase;
   D. reacting the solid phase with a cleaving agent that selectively removes the covalently bound monitoring agent from the amino ends of the unreacted peptide chains while leaving the blocked amino termini and the peptide chains intact, said monitoring agent not being the same as or similar to said blocking agent of the first step, such that said cleaving agent will cleave said monitoring agent but not said blocking agent;
   E. measuring quantitatively the amount of the monitoring agent removed; and
   F. depending upon the number of unreacted peptide chains, as determined by the quantitative measurement of said removed monitoring agent, either
      1. repeating the process with the same blocked amino acid or;
      2. removing the blocking agent from the terminal amino group and repeating the process with a subsequent blocked amino acid in the peptide sequence.

2. The method according to claim 1 wherein the monitoring agent is a trityl (triphenylmethyl) -based groups.

3. The method according to claim 2 wherein the trityl-based group is a trityl, monomethoxytrityl, dimethoxytrityl, or trimethoxytrityl group.

4. The method according to claim 2 wherein the trityl-based group is generated from a trityl-based compound selected from the group consisting of trityl-based halides, trityl-based carboxylates, and trityl-based acid anions.

5. The method according to claim 2 wherein the trityl-based group is generated from a trityl-based compound selected from the group consisting of trityl chloride, monomethoxytrityl chloride, dimethoxytrityl chloride, and trimethoxytrityl chloride.

6. The method according to claim 3 wherein the monitoring agent is dissolved in a basic reaction solution and the cleaving reagent is an acidic solution.

7. The method according to claim 6 wherein the basic reaction solution comprises diisopropylethylamine; and the cleaving reagent comprises trichloroacetic acid.

8. The method according to claim 1 wherein
   A. the monitoring agent is dimethoxytrityl chloride dissolved in a reaction solution comprising diisopropylethylamine;
   B. the washing solution comprises hydroxybenzotriazole and trifluoroethanol; and
   C. the cleaving reagent comprises trichloroacetic acid and a carbonium ion scavenger.

9. The method according to claim 8 wherein the carbonium ion scavenger is anisole.

10. The method according to claim 1 wherein
    A. the monitoring agent is monomethoxytrityl chloride dissolved in a reaction solution comprising diisopropylethylamine;
    B. the washing solution comprises hydroxybenzotriazole and trifluoroethanol; and
    C. the cleaving reagent comprises trichloroacetic acid and a carbonium ion scavenger.

11. The method according to claim 10 wherein the carbonium ion scavenger is anisole.

12. The method according to claim 1 wherein

A. the monitoring agent is trimethoxytrityl chloride dissolved in a reaction solution comprising diisopropylethylamine;
B. the washing solution comprises methylene chloride; and
C. the cleaving reagent comprises trichloroacetic acid and a carbonium ion scavenger.

13. The method according to claim 12 wherein the carbonium ion scavenger is anisole.

14. The method according to claim 1 wherein
A. the monitoring agent is trityl chloride dissolved in a reaction solution comprising diisopropylethylamine;
B. the washing solution comprises dimethylformamide; and
C. the cleaving reagent comprises trichloroacetic acid.

15. A process as defined in claim 1 wherein step F.2. further includes the addition of a capping agent prior to removing said blocking agent from the terminal amino group.

16. A process for monitoring a solid-phase peptide synthesis for free amino ends of unreacted peptide chains, comprising:
A. synthesizing a peptide chain by adding a blocked amino acid, comprising an amino acid bound to a blocking agent, to a peptide chain that is anchored to the solid-phase;
B. reacting the solid phase with a monitoring agent that forms a covalent bond with amino groups under reaction conditions that promote such covalent bonding.
C. washing the solid phase with a washing solution to remove non-covalently bound monitoring agent from the solid phase;
D. reacting the solid phase with a cleaving agent that selectively removes the covalently bound monitoring agent from the amino ends of the unreacted peptide chains while leaving the blocked amino termini and the peptide chains intact, said monitoring agent not being the same as or similar to said blocking agent of the first step, such that said cleaving agent will cleave said monitoring agent but not said blocking agent;
E. measuring quantitatively the amount of the monitoring agent removed; and
F. depending upon the number of unreacted peptide chains, as determined by the quantitative measurement of said removed monitoring agent, either
  1. repeating the process with the same blocked amino acid or;
  2. removing the blocking agent from the terminal amino group and repeating the process with a subsequent blocked amino acid in the peptide sequence or;
  3. adding a capping agent to prevent the subsequent elongation of the unblocked chains and thereby terminate their growth and then performing step F.2.

* * * * *